US010816440B2

(12) United States Patent
Amendt et al.

(10) Patent No.: US 10,816,440 B2
(45) Date of Patent: Oct. 27, 2020

(54) ROCK MECHANICAL PROPERTIES FROM DRILL CUTTINGS

(71) Applicant: CONOCOPHILLIPS COMPANY, Houston, TX (US)

(72) Inventors: David V. Amendt, Calgary (CA); Seth Busetti, Houston, TX (US); William R. Morris, Houston, TX (US); Eric Cline, Olympia, WA (US); Fabian Duque-Botero, Boynton Beach, FL (US); Peter S. D'Onfro, Katy, TX (US); Peter H. Hennings, West Lake Hills, TX (US)

(73) Assignee: CONOCOPHILLIPS COMPANY, Houston, TX (US)

( * ) Notice: Subject to any disclaimer, the term of this patent is extended or adjusted under 35 U.S.C. 154(b) by 153 days.

(21) Appl. No.: 15/886,344

(22) Filed: Feb. 1, 2018

(65) Prior Publication Data
US 2018/0238774 A1 Aug. 23, 2018

Related U.S. Application Data

(60) Provisional application No. 62/461,051, filed on Feb. 20, 2017.

(51) Int. Cl.
 G01N 1/08 (2006.01)
 G01N 3/08 (2006.01)
 (Continued)

(52) U.S. Cl.
 CPC ............ *G01N 1/08* (2013.01); *E21B 49/005* (2013.01); *G01N 3/00* (2013.01); *G01N 3/08* (2013.01);
 (Continued)

(58) Field of Classification Search
 CPC ............ G01N 1/08; G01N 3/08; G01N 33/24
 See application file for complete search history.

(56) References Cited

U.S. PATENT DOCUMENTS

2014/0373616 A1* 12/2014 Amendt .................. E21B 47/00
  73/152.01
2015/0152724 A1* 6/2015 Amendt .................. G01N 1/04
  73/152.01
2017/0022808 A1* 1/2017 Busetti .................. E21B 49/087

FOREIGN PATENT DOCUMENTS

CN 103278614 B 7/2015

OTHER PUBLICATIONS

Willis, M., "Upscaling anisotropic geomechanical properties using Backus averaging and petrophysical clusters in the Vaca Muerta formation. Colorado School of Mines", 2013, ProQuest Dissertations Publishing, (20140000), XP055533552;167 pgs.

* cited by examiner

*Primary Examiner* — Jamel E Williams
(74) *Attorney, Agent, or Firm* — ConocoPhillips Company

(57) ABSTRACT

This disclosure describes a novel method for predicting or estimating rock mechanical properties from cuttings at a particular depth based on determining the facies, plotting the facies on a ternary diagram with clay, silica and carbonate endpoints, and estimating rock mechanical properties based on comparison to a database of core samples from vertical wells that is also organized by depth and facies. We have shown that datapoints at similar locations on the ternary diagram will have fairly similar rock properties. These rock properties can be used to improve the reliability of a variety of reservoir modeling platforms, which can then be used in designing and implementing completion, stimulation and production plans.

11 Claims, 3 Drawing Sheets

Ternary Diagram with Composition Units

(51) Int. Cl.
   *G01N 33/24*   (2006.01)
   *E21B 49/00*   (2006.01)
   *G01N 3/00*    (2006.01)
   *G06F 30/20*   (2020.01)
   *G01V 99/00*       (2009.01)

(52) U.S. Cl.
   CPC .............. *G01N 33/24* (2013.01); *G06F 30/20* (2020.01); *G01N 2203/0053* (2013.01); *G01N 2203/0067* (2013.01); *G01N 2203/0218* (2013.01); *G01V 99/00* (2013.01); *G01V 2210/6242* (2013.01)

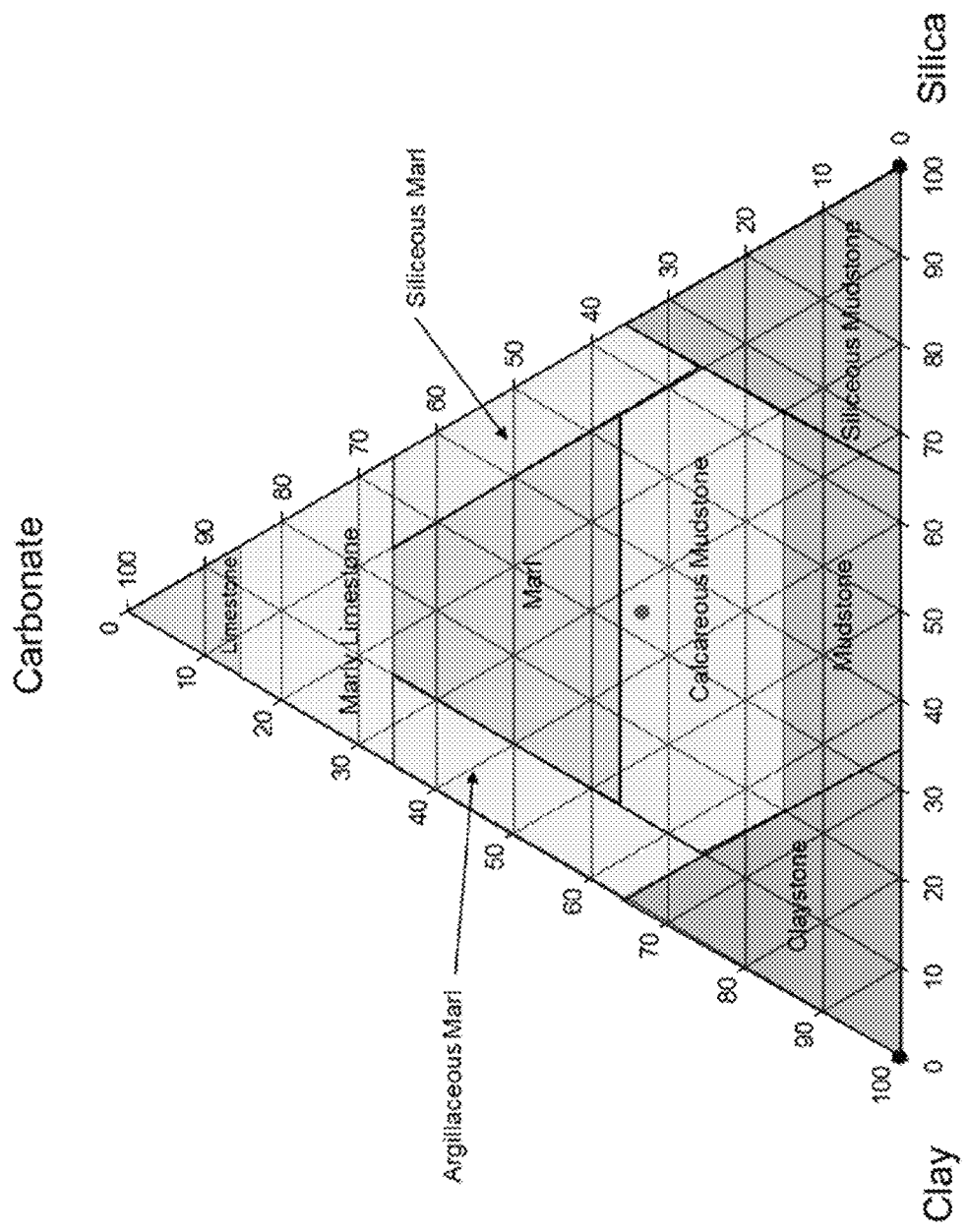
Figure 1: Ternary Diagram with Composition Units

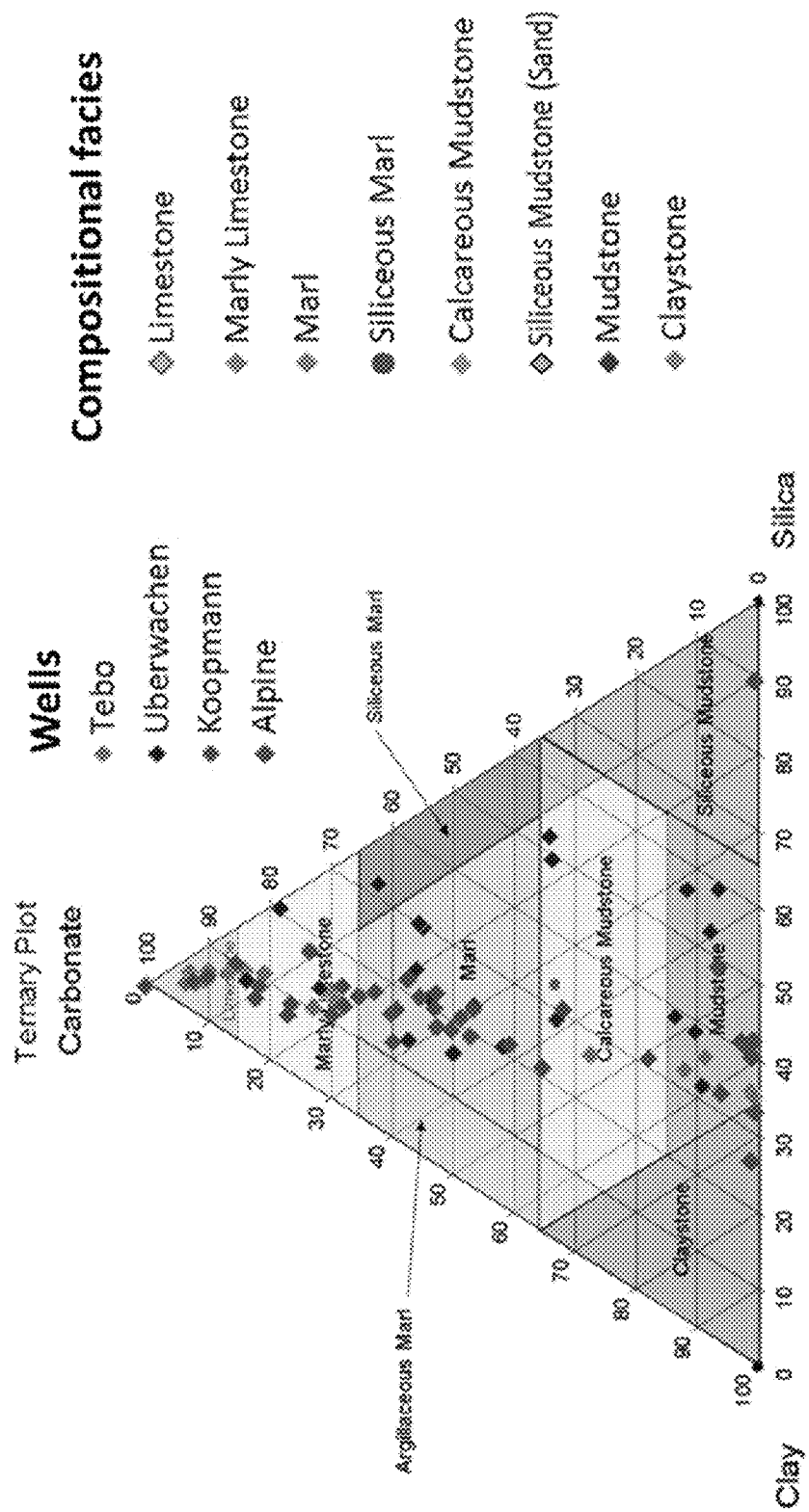
Figure 2: Ternary Diagram populated with XRD data from various Mechanical Bulk Samples

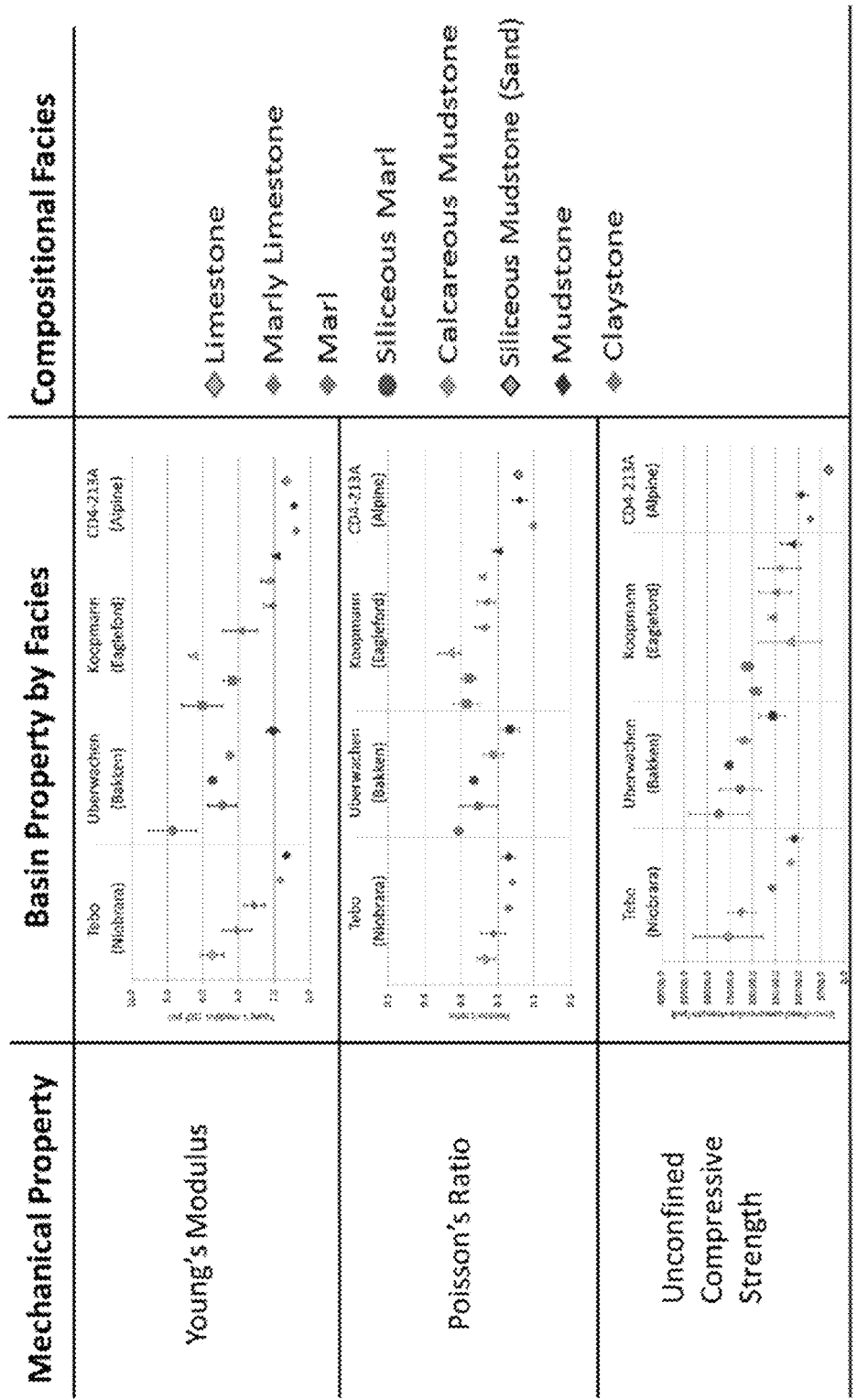
Figure 3: Graphical representation of a mechanical characterization by facies for 4 different basins: Niobrara, Bakken, Eagleford & Alpine

ROCK MECHANICAL PROPERTIES FROM DRILL CUTTINGS

PRIOR RELATED APPLICATIONS

This application is a non-provisional application which claims benefit under 35 USC § 119(e) to U.S. Provisional Application Ser. No. 62/461,051 filed Feb. 20, 2017, entitled "ROCK MECHANICAL PROPERTIES FROM DRILL CUTTINGS," which is incorporated herein in its entirety.

FIELD OF THE DISCLOSURE

The disclosure generally relates to a method of estimating rock mechanical properties from wellbore drill cuttings using the compositional facies of the cuttings. The estimates are obtained by comparison with a library of rock mechanical data that is also organized by depth and compositional facies and obtained by conventional analysis of cores from offset vertical wells or other sources. Cuttings are assigned the rock properties that were obtained by those core samples having the same compositional facies and depth as the cuttings.

BACKGROUND OF THE DISCLOSURE

A critical tool for modern oil and gas exploration and production is the reservoir simulator. There are three basic components required for a simulation study. These are:
  The tool: reservoir simulator—software used to model the reservoir.
  The pertinent information: a description of the reservoir
  The intelligent user: an experienced simulation engineer
The tool is only as good as the assumptions inputted into the software, and thus detailed chemical, geologic, mechanical, and geophysical information about the reservoir is important for establishing the correct or best assumptions for the model. As field development progresses, more information becomes available, enabling the simulation engineer to continually refine the reservoir description, thus improving the modeling, and thereby improving the results.

Conventional techniques for determining mechanical properties along a wellbore include cutting a core and running wireline logs using sonic logging techniques. The rock mechanical model serves calibration needs for 1) elastic stress modeling—using a CHILE (Continuous Homogeneous Isotropic Linearly Elastic) subsurface material medium; or 2) geologically based stress modeling—using a DIANE (Discontinuous Inhomogeneous Anisotropic Non Elastic) subsurface material medium.

The CHILE model is useful for man-made construction materials, such as steel and concrete, because these materials are generally homogeneous, isotropic, linearly elastic and without defect. However, the model is quite limited in natural rock, where in homogeneities are the norm.

The DIANE material model is therefore the more realistic subsurface earth model. Ideally it captures the geological heterogeneities responsible for creating the discontinuous, inhomogeneous, anisotropic and non-elastic nature of the subsurface reservoir. A DIANE subsurface model can be created using a mechanical facies model and the principles of mechanical stratigraphy. However, the DIANE model currently lacks wellbore data that links back to the rock type property description and depositional environment.

Typically, rock properties are determined from core testing and linked back to a predictive model using wireline or logging while drilling ("LWD") log data and the elastic model—assuming a CHILE subsurface. Using these techniques, the elastic and failure properties can be estimated, but the uncertainty remains high. Static to dynamic transforms of elastic properties have scalability issues and linear transforms for Poisson's ratio do not exist at the plug scale.

Furthermore, in horizontal wells—which are commonly used for unconventional plays—coring is a rare occurrence because of considerable additional risk and cost in performing such a procedure in a horizontal well. Running wireline logs in horizontal wells is also risky—it is rarely performed because of additional service cost, the increased risk of non-productive drilling time due to tool failure and the increased potential for hole collapse.

Logging tools (both wireline and LWD) were originally designed to run in vertical wells, therefore horizontal well logging and interpretation typically carries high uncertainty and high risk. The interpreted mechanical products from both LWD and wireline sonic technologies have high uncertainties due to parallel bedding tool physics issues and unpredictable compressional and shear wave polarizations in horizontal wells. Thus, despite success in conventional reservoirs, the sonic-based approach has not been accurate or reliable on many non-conventional rock layers, such as shale, mudstone or marl, which are strongly heterogeneous, exhibit ductile behavior and are often developed using horizontal drilling.

Research has been published attempting to empirically correlate mineralogy to mechanical properties for different rock formation, but have been less than satisfactory to date. Thus, what is needed in the art are better methods of determining the mechanical properties of rock in a horizontal well, without significantly increasing drilling risk and cost. A better description of the mechanical properties of the reservoir will allow better reservoir simulation, and better decisions regarding the development and production of hydrocarbons, such as heavy oil, shale oil, gas and the like.

SUMMARY OF THE DISCLOSURE

This invention was created to address the problem of trying to determine the mechanical rock properties along a horizontal wellbore, without significantly increasing drilling risk and cost. By linking cuttings analysis to a compositional facies model and mechanically characterizing the same compositional facies elements using whole core from vertical pilot wells, we eliminate the need, risk and cost to run horizontal LWD and wireline sonic logs for geomechanical purposes. The methods described herein utilize the rock fragments that already come to surface in every wellbore drilled, without directly interfering with the drilling operation itself. Thus, drilling efficiency is not sacrificed because no new operational procedure is needed.

In more detail, the methodology estimates rock mechanical properties from wellbore drill cuttings, by comparison to a database of core samples that are analyzed by traditional methods. Wellbore drill cuttings are collected, depth referenced and analyzed for mineral composition, using e.g., XRD, XRF or other technology. The data from each sample is plotted on a percentage basis on a ternary diagram with silicate, carbonate and clay endpoints.

The ternary diagram, commonly used for shales, mudstones, and unconventional or source rock types, is currently subdivided into nine compositional facies that are defined by prescribed ratios of the three primary elements. The percentage ratios of silicate, carbonate and clay are plotted on the ternary diagram to determine the compositional facies for each cutting sample. The current nine compositional facies include: (1) Limestone, (2) Marly Limestone, (3) Argillaceous Limestone, (4) Marl, (5) Siliceous Marl, (6) Claystone, (7) Calcareous Mudstone, (8) Siliceous Mudstone & (9) Mudstone.

In a separate analysis process, whole core from e.g., nearby vertical pilot wells are characterized for both rock mechanical characteristics, as well as compositional facies (e.g., mineral composition) and depth. Mechanical rock properties from similar rock types are grouped using the ternary facies model, preferably grouped into the current nine subdivisions, but other groupings may be possible. The grouped rock mechanical test results provide normal distributions of material properties by facies type. The mean values with standard deviations for: Young's modulus, Poisson's ratio, unconfined compressive strength, friction angle, cohesion and tensile strength are reported and archived for each compositional facies and depth. Additional mechanical rock properties can be included based on application need.

The cuttings data are then compared against the database data, and rock properties from the database assigned to the cuttings based on selecting those database values with the same or similar compositional facies and depth.

To date, a substantial database of rock mechanical properties from core samples around the world has been created and organized by drilling region and basin. For each core, the mechanical properties have been cataloged based on the compositional facies model from the prescribed ternary diagram as well as depth. The library of material properties, organized by compositional facies and depth, continues to expand as new cores are added.

The drill cuttings are analyzed to derive a mechanical property log using the compositional facies classification system. This system generates a lithological facies log, characterized by separate stratigraphic units that are determined by geologic characterization which typically includes unique mineralogy. Next, the appropriate mechanical properties, including but not limited to Young's modulus, Poisson's ratio, uniaxial compressive strength, and the like, are assigned to each facies. This is in contrast to a continuous electrical facies log, such as a sonic log, which detects petrophysical parameters over an averaging window and then uses idealized rock physics theoretical or empirical equations to model rock properties, independent of the facies classification.

Our method produces a 1D mechanical well model with elastic and failure properties for engineering design and wellbore performance diagnostics. The mechanical facies characterization technique promotes the development of mechanical stratigraphy models that provide a method to access realistic large-scale rock heterogeneities that influence wellbore performance. The geological heterogeneities associated with rock type variations, stratigraphic and depositional characteristics and structural attributes including natural faults and fractures can be systematically included in the analysis.

In more detail, the method involves:
(1) obtaining a plurality of rock cutting samples from a reservoir at a depth D1-Dn, wherein n is the number of samples, and D is the depth of each sample;
(2) measuring a percentage content of silica, clay and carbonate of each of said cutting samples;
(3) plotting said percentage content of silica, clay and carbonate of each of said samples on a ternary diagram for each depth D 1-Dn, said ternary diagram having 0-100% of silica, clay and carbonate at the vertices or performing an equivalent technique;
(4) comparing against a database of rock mechanical properties obtained by measuring a plurality of core samples, preferably from nearby vertical wells, said database also organized by depth and by percentage content of silica, clay and carbonate; and
(5) estimating rock mechanical properties of said cutting samples from core samples having a similar depth and a similar percentage content of silica, clay and carbonate.

Preferably, the original cutting samples are from horizontal wells, in unconventional plays, and the core samples from nearby vertical wells, although the database is preferably a global database. The database can be pre-collected, but can be continuously updated as more and more core data is accumulated. In one embodiment, the data in the ternary plot is further subdivided according to mineral content, and we have provided one example of a subdivision herein.

Of course, the ternary plots need not be actually graphed, and other equivalent mathematical or organizational methods could be used. For example, the sample data can be directly compared against a database of core data that is also organized by depth and compositional facies or percentage content of silica, clay and carbonate. In other embodiments, a ternary plot or a ternary plot-like organizational mechanism is used to subdivide the data according to the core data from various basins.

The present disclosure also relates to a computing apparatus for performing certain operations herein and the same or a separate computing apparatus for hosting the database. This apparatus may be specially constructed for the required purposes of modeling, or it may comprise a general-purpose computer selectively activated or reconfigured by a spreadsheet program and reservoir simulation computer program stored in the computer. Such computer programs may be stored in a computer readable storage medium, preferably non-transitory, such as, but is not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions, each coupled to a computer system bus.

In one embodiment, the computer system or apparatus may include graphical user interface (GUI) components such as a graphics display and a keyboard, which can include a pointing device (e.g., a mouse, trackball, or the like, not shown) to enable interactive operation. The GUI components may be used both to display data and processed data and to allow the user to select among options for implementing aspects of the method or for adding information about reservoir inputs or parameters to the computer programs. The computer system may store the results of the system and methods described above on disk storage, for later use and further interpretation and analysis. Additionally, the computer system may include on or more processors for running said spreadsheet and simulation programs.

Hardware for implementing the inventive methods may preferably include massively parallel and distributed Linux clusters, which utilize both CPU and GPU architectures. Alternatively, the hardware may use a LINUX OS, XML universal interface run with supercomputing facilities provided by Linux Networx, including the next-generation Clusterworx Advanced cluster management system.

Another system is the Microsoft Windows 7 Enterprise or Ultimate Edition (64-bit, SP1) with Dual quad-core or hex-core processor, 64 GB RAM memory with Fast rotational speed hard disk (10,000-15,000 rpm) or solid state drive (300 GB) with NVIDIA Quadro K5000 graphics card and multiple high resolution monitors.

Slower systems could also be used, but are less preferred because the method is already compute intensive.

In other embodiments, the invention is a system comprising one or more non-transitory machine-readable storage mediums, which when executed by at least one processor of a computer, performs at least some of steps of the method(s) described herein, and stores the database described herein. These can be the same computer, or different computers, and in other embodiments the database is reached via the internet or other network.

The term "many-core" as used herein denotes a computer architectural design whose cores include CPUs and GPUs. Generally, the term "cores" has been applied to measure how many CPUs are on a giving computer chip. However, graphic cores are now being used to offset the work of CPUs. Essentially, many-core processors use both computer and graphic processing units as cores.

The invention includes any one or more of the following embodiments, in any combination(s) thereof:

A method of estimating rock properties, said method comprising:
a. obtaining a plurality of rock cutting samples from a reservoir at a depth D1-Dn, wherein n is the number of cutting samples, and D is the depth of each cutting sample;
b. measuring a percentage content of silica, clay and carbonate of each of said cutting samples;
c. comparing against a database of rock mechanical properties obtained by measuring a plurality of core samples, said database organized by depth and by percentage content of silica, clay and carbonate; and
d. estimating rock mechanical properties of said cutting samples from said database by selecting core samples having a similar depth and a similar percentage content of silica, clay and carbonate and assigning rock mechanical properties from said selected core samples to said cutting samples.
Any method herein described, further including grouping data into compositional facies based on the percentage content of silica, clay and carbonate and constructing a 1D property log wherein the compositional facies are assigned to each depth, and each compositional facies is populated with the assigned rock mechanical property for that compositional facies.
Any method herein described, wherein said cutting samples are obtained from horizontal wells.
Any method herein described, wherein said core samples are obtained from nearby vertical wells.
Any method herein described, wherein said core samples were obtained from nearby vertical wells before step a) or at about the same time as step a).
Any method herein described, wherein said rock mechanical properties include 1, 2, 3, 4 or more or all of Young's modulus, Poisson's ratio, unconfined compressive strength, friction angle, cohesion, tensile strength, fracture toughness, peak strength, and compressibility.
Any method herein described, further comprising inputting said rock mechanical properties of said samples into a reservoir modeling program to predict reservoir performance and optimize a reservoir production plan.
Any method herein described, further comprising using the optimized reservoir production plan to produce oil from said reservoir.
Any method herein described, further including the step of plotting said percentage content of silica, clay and carbonate of said samples on a ternary diagram or its equivalent for each sample, said ternary diagram having 0-100% of silica, clay and carbonate at the vertices and assigning a compositional facies based on where a sample falls on the ternary plot or its equivalent, wherein said ternary diagram is subdivided into nine compositional facies using the following cutoffs:
   1. Limestone >85 Carbonate
   2. Marly Limestone >65% Carbonate <85%
   3. Argillaceous Marl >35% Clay, <65% Carbonate>35%, <10% Silica
   4. Marl >35% Carbonate<65%, >10% Silica >10% Clay
   5. Siliceous Marl >35% Silica, <65% Carbonate>35%, <10% Clay
   6. Claystone >65% Clay
   7. Calcareous Mudstone <35% Carbonate >15%, >10% Silica<65%, >10% Clay <65%)
   8. Siliceous Mudstone >65% Silica
   9. Mudstone <15% Carbonate, <65% Silica, <65% Clay.
Any method herein described, wherein data from said core samples is also grouped into said nine composition facies.
A method of estimating rock properties, said method comprising:
obtaining a plurality of rock cutting samples from horizontal wells in a reservoir at a depth D1-Dn, wherein n is the number of samples, and D is the depth of each sample;
measuring a percentage content of silica, clay and carbonate of each of said samples;
plotting said percentage content of silica, clay and carbonate of said samples on a ternary diagram or its equivalent for each sample, representing a particular depth, D, said ternary diagram having 0-100% of silica, clay and carbonate at the vertices, wherein said ternary diagram is subdivided into nine composition facies using approximately (+/−3%) or exactly the following cutoffs:
   • Limestone >85 Carbonate
   • Marly Limestone >65% Carbonate <85%
   • Argillaceous Marl >35% Clay, <65% Carbonate>35%, <10% Silica
   • Marl >35% Carbonate<65%, >10% Silica >10% Clay
   • Siliceous Marl >35% Silica, <65% Carbonate>35%, <10% Clay
   • Claystone >65% Clay
   • Calcareous Mudstone <35% Carbonate >15%, >10% Silica<65%, >10% Clay <65%)
   • Siliceous Mudstone >65% Silica
   • Mudstone <15% Carbonate, <65% Silica, <65% Clay.
comparing against a database of rock mechanical properties obtained by measuring a plurality of core samples from offset vertical wells in said reservoir, said database organized by depth and by said nine compositional facies; and
estimating rock mechanical properties of said samples from core samples having the same depth and same compositional facies.
Any method herein described, further comprising inputting said 1D property log into a reservoir modeling program to predict reservoir performance and optimize a reservoir production plan.

-continued

Any method described herein, including the further step of printing, displaying or saving the results of the method.

A printout or 3D display of the results of the method.

A non-transitory machine-readable storage medium containing or having saved thereto the results of the method.

A non-transitory machine-readable storage medium having saved thereto software to perform the method, and a separate or the same non-transitory machine-readable storage medium having saved thereto the database used in the method.

Any method described herein, further including the step of using said results in a reservoir modeling program to predict reservoir performance characteristics, such as fracturing, production rates, total production levels, rock failures, faults, wellbore failure, and the like.

Any method described herein, further including the step of using said results to design and implement a reservoir drilling, development, production and/or stimulation program.

A non-transitory machine-readable storage medium, which when executed by at least one processor of a computer, performs at least some of steps of the method(s) described herein.

As used herein, the term "facies" in geology means a body of rock with specified characteristics, which can be any observable attribute of rocks such as their overall appearance, composition, or condition of formation, and the changes that may occur in those attributes over a geographic area.

As used herein, the term "compositional facies" refers to the composition of a body of rock, e.g., the percentage content of silica, clay and carbonate.

As used herein, the term "ternary plot" refers to a three-axis graph with 0-100% silica, clay and carbonate at the vertices. However, there are mathematical and organizational equivalents to actually providing this graph, and such equivalents are included in the scope of the term. Thus, "plotting a ternary plot" is intended to non-graph equivalents.

As used herein, the term "core" or "core sample" means a typically cylindrical section of (usually) a naturally occurring substance. Most core samples are obtained by drilling with special drills into the substance, for example sediment or rock, with a hollow steel tube called a core drill. The hole made for the core sample is called the "core bowling". A variety of core samplers exist to sample different media under different conditions. More continue to be invented on a regular basis. In the coring process, the sample is pushed more or less intact into the tube. Removed from the tube in the laboratory, it is inspected and analyzed by different techniques and equipment depending on the type of data desired.

As used herein, the term "cutting" or "cutting sample" means the irregular rock fragments produced during drilling by the drill bit.

As used herein, "rock mechanical data" or "rock mechanical properties" means characterization of the mechanical properties of a given rock type. Such characterization includes, e.g., density, Young's modulus (aka elastic modulus—resistance to being deformed elastically (i.e., non-permanently) when a force is applied), shear modulus (ratio of shearing (torsional) stress to shearing strain), bulk modulus (change in volume under hydrostatic pressure), fracture gradient (formation fracturing pressure as a function of well depth in units of psi/ft), formation strength, Poisson's ratio (ratio of the proportional decrease in a lateral measurement to the proportional increase in length in a sample of material that is elastically stretched), unconfined compressive strength (maximum axial compressive stress that a right-cylindrical sample of material can withstand when the confining stress is zero), cohesion (component of shear strength of a rock or soil that is independent of interparticle friction), friction angle (a shear strength parameter), tensile strength (resistance to stress which stretches rocks in opposite directions), fracture toughness (the critical stress intensity factor at a crack needed to induce fracturing), peak strength (the maximum axial compressive stress that a right-cylindrical sample of material can with stand under a pre-determined confining stress), compressibility (the relative change in pore volume per unit change in pressure), and the like.

As used herein, the term "material property log" or "1D property log" or similar phase means a one-dimensional continuous physical characterization of the geologic formation, generally including the rock mechanical properties described herein, as well as mineral composition and any other parameters (like texture) that are inputted into the method.

The use of the word "a" or "an" when used in conjunction with the term "comprising" in the claims or the specification means one or more than one, unless the context dictates otherwise.

The term "about" means the stated value plus or minus the margin of error of measurement or plus or minus 10% if no method of measurement is indicated.

The use of the term "or" in the claims is used to mean "and/or" unless explicitly indicated to refer to alternatives only or if the alternatives are mutually exclusive.

The terms "comprise", "have", "include" and "contain" (and their variants) are open-ended linking verbs and allow the addition of other elements when used in a claim.

The phrase "consisting of" is closed, and excludes all additional elements.

The phrase "consisting essentially of" excludes additional material elements, but allows the inclusions of non-material elements that do not substantially change the nature of the invention.

The following abbreviations are used herein:

| ABBREVIATION | TERM |
| --- | --- |
| XRD | x-ray diffraction |
| TVD | true vertical depth |
| GR | Gamma ray |
| XRF | X-ray fluorescence |
| LWD | Logging while drilling |

BRIEF DESCRIPTION OF THE DRAWINGS

FIG. 1 is a ternary diagram showing percent clay, silica and carbonate. The diagram is further subdivided into 9 types of rock, depending on the relative percentages of these three minerals.

FIG. 2 shows the ternary diagram overwritten with XRD data from various mechanical bulk samples taken from real wells. The data shows a broad compositional distribution across multiple facies categories, with multiple data points in each group. This indicates that the sample data is sufficiently robust to be used for characterizing rock properties.

FIG. 3 shows a graphical representation of a mechanical characterization by facies for 4 different basins: Niobrara, Bakken, Eagleford & Alpine. The mechanical properties vary by compositional facies, but are predictable within a basin, falling within a predictable range based on the bulk sample mechanical test results. Further, the error bars are not large, indicating that uncertainties are better than heretofore available. This indicates that rock mechanical properties can be predicted based on the compositional facies descriptions that are determined from rock cuttings, as compared to a library of core data previously compiled and organized by depth and compositional facies. Because the cuttings are readily available along the entire length of a horizontal well, a great deal more information is thereby made available than was previously available. This information can be used in various reservoir modeling programs, thereby improving results and maximizing efficiency of hydrocarbon production.

DETAILED DESCRIPTION

Rock mechanical properties are a fundamental input for reservoir modeling. Current means to determine mechanical properties from logs is not accurate in shale gas systems. Therefore, if a quantitative link between compositional facies of cuttings and their mechanical properties can be established, models will be improved and well-drilling can be more efficiently accomplished and oil production and/or efficiencies maximized.

This invention provides systems and methods for determining rock mechanical properties from drill cuttings. The workflow is an integration of five distinct analysis steps, not necessarily performed in the provided order (e.g., the library may already be available, especially as the method gains acceptance and more and more data is accumulated):

1. Determining Rock Composition (% clay, silica and carbonate) from wellbore cuttings in a well of interest.
2. Developing and deploying a prescribed compositional facies model to suitably group data.
3. Perform rock mechanical characterization of whole core from nearby offset vertical wells. Also determine the rock composition (% clay, silica and carbonate) of the same core samples.
4. Create a library of quality controlled rock mechanical properties, organized by composition facies and depth from the core samples analyzed in step 3. Continually update this database, including data from around the globe.
5. Compare the cuttings compositional facies against the database of compositional facies at a given depth, and estimate rock mechanical properties from the nearest datapoints in the database.
6. Build a material property log using petrophysical characterization techniques, specifically, using automated software to correlate mineral composition of cuttings to the empirical property definitions.

1. Determining Rock Composition from Wellbore Cuttings

All wells drilled in the oil and gas industry create wellbore drill cuttings that are circulated to surface during the drilling process. The cuttings are carried to surface in the returning drilling fluid and separated from the drill mud before the fluid is pumped back to the bit. The cuttings pile up next to the shale shaker and samples are collected at regular intervals by the mud logger or wellsite geologist. The samples are lag corrected and depth labelled for further analysis. The act of collecting the cutting samples in no way interferes with or delays the drilling process—the cuttings are produced in the act of drilling the well.

The cuttings can be analyzed for a variety of applications. Core bit cuttings (currently being tested in unconventional horizontal wells) produce larger chunks of rock from which thin sections, SEM and capillary pressure tests can be made. Finer grained rock cuttings can be analyzed for geochemical composition and mineral composition using various measurement techniques.

For our purposes, cuttings are analyzed using XRD, XRF or any other industry or vendor technique to determine the basic mineral composition (% clay, silica and carbonate). With those three parameters (% Silicate, % Carbonate & % Clay) we are able to determine the compositional facies using the prescribed mudstone ternary diagram described in section 2.

2. Developing and Deploying a Prescribed Compositional Facies Model to Suitably Group Data With the percentage of silicate, carbonate and clay ratios, the compositional facies are assigned using e.g., a mudstone ternary diagram. The ternary diagram is a triangle having three axes, with silicate, carbonate and clay vertices and the axes range from 0-100%. These mineral endpoints were chosen because they represent the primary compositional elements present in most of the unconventional organic mudrock plays that have been discovered so far. However, in other types of plays, it is possible that the endpoints might vary.

For example, mudstones typically include clay and silt sized particles. In most cases minor sand size particles will be present and cannot be separate by XRD and XRF analysis, thus visual estimation of silt and sand sized particles may be necessary. When visual grain size data is included, the above ternary diagram can be further modified by silt and sand (a mudstone can be described as a silty (25-50% silt) mudstone or a muddy siltstone (50-75% silt). This modification of terminology has only been used for terrigeneous mudstone systems and biogenic silicic and mixed biogenic silicic systems. One could, for example, extend the triangle in a third dimension like a pyramid, technically a tetrahedra, or one could just further subdivide the silica section.

The ternary diagram (see FIG. 1) can be subdivided into nine composition facies using the following approximate cutoffs:

1. Limestone→85 Carbonate
2. Marly Limestone→65% Carbonate <85%
3. Argillaceous Marl→35% Clay, <65% Carbonate >35%, <10% Silica
4. Marl→35% Carbonate <65%, >10% Silica >10% Clay
5. Siliceous Marl→35% Silica, <65% Carbonate >35%, <10% Clay
6. Claystone→65% Clay
7. Calcareous Mudstone-<35% Carbonate >15%, >10% Silica <65%, >10% Clay <65%)
8. Siliceous Mudstone→65% Silica
9. Mudstone-<15% Carbonate, <65% Silica, <65% Clay However, these cutoffs are exemplary only, and one may choose to vary the cutoffs differently under different conditions.

The compositional facies categories are data driven with fixed boundary value cutoffs in our example. True mechanical facies would, however, include texture elements and other geological controls. However, we have used simpler geological models (like the mudstone ternary facies model) in our proof of concept work because they are reproducible and predictable with basic measurement technology. We thus created the facies model foundational framework with compositional analysis only in the early stages of our subsurface characterization. Textural features will be assessed during the application development phase and be included in the evolving facies model as required. As our understanding of the mechanical response mechanisms increases, detailed composition and texture models will emerge.

Other geological heterogeneities that influence rock mechanical properties like: fractures, faults, laminations, inter-bedding planes of weakness or other foliation planes can be included the development of a mechanical stratigraphy model. The mechanical stratigraphy model is an example of a geologically conditioned 'Geomechanical application' of the rock mechanical property log created from drill cuttings.

3. Rock Mechanical Characterization and Mineral Analysis of Offset Cores

A core is obtained from a nearby vertical well and used to determine both mineral content (% clay, silica and carbonate), as well as rock mechanical properties. Any method of core testing can be used to generate mechanical data including, for example, Young's Modulus, Poisson's Ratio, Unconfined Compressive Strength, Cohesion, Friction Angle and Tensile strength. In addition, compositional facies for each core sample is determined. Of course, to the extent that a basin has already been studied, this data may already be available and cataloged in the database.

Preferably, the method uses the improved methods described in US20150152724 and US20140373616, thus resulting in better, quality controlled data. However, other methods of analysis could be used.

Such methods include, for example, X-ray diffraction or "XRD", which can distinguish the major, minor, and trace compounds present in a sample. XRD is the primary, non-destructive tool for identifying and quantifying the mineralogy of crystalline compounds in rocks, soils and particulates. Every mineral or compound has a characteristic X-ray diffraction pattern whose "fingerprint" can be matched against a database of over 250000 recorded phases. Modern computer-controlled diffraction systems can interpret the diffraction traces produced by individual constituents and highly complex mixtures. The data usually includes mineral (common) name of the substance, chemical formula, crystalline system, and reference pattern number from the ICDD International database.

X-ray fluorescence or "XRF" is another common technique. An XRF spectrometer works on wavelength-dispersive spectroscopic principles that are similar to an electron microprobe (EPMA). The analysis of major and trace elements in geological materials by x-ray fluorescence is made possible by the behavior of atoms when they interact with radiation. When materials are excited with high-energy, short wavelength radiation (e.g., X-rays), they can become ionized. If the energy of the radiation is sufficient to dislodge a tightly-held inner electron, the atom becomes unstable and an outer electron replaces the missing inner electron. When this happens, energy is released due to the decreased binding energy of the inner electron orbital compared with an outer one. The emitted radiation is of lower energy than the primary incident X-rays and is termed fluorescent radiation. Because the energy of the emitted photon is characteristic of a transition between specific electron orbitals in a particular element, the resulting fluorescent X-rays can be used to detect the abundances of elements that are present in the sample.

Yet another method is instrumental neutron activation analysis (INAA) is used to determine the concentration of trace and major elements in a variety of matrices. A sample is subjected to a neutron flux and radioactive nuclides are produced. As these radioactive nuclides decay, they emit gamma rays whose energies are characteristic for each nuclide. Comparison of the intensity of these gamma rays with those emitted by a standard permit a quantitative measure of the concentrations of the various nuclides.

Other methods include mass spectrometry, micro-imaging instruments, such as the Petrographic Microscope, X-ray Computed Tomography (CT); Scanning Electron Microscopy (SEM); SEM-Cathodoluminescence (SEM-CL); Optical Cathodoluminescence (Op-CL); surface spectroscopies such as Time Of Flight-Secondary Ion Mass Spectrometry (ToF-SIMS), and the like. Hyperspectral core imaging system (HCIS) has also been used to determine rock composition using high resolution RGB or color photograph spectrometry, as well as short wave infrared (SWIR) and long wave infrared spectrometry.

4. Create a Library of Rock Mechanical Properties Organized by Compositional Facies and Depth A library of material properties that is organized by compositional facies and depth for the various basins where cores have already been tested is created. To date we have a library of data from core samples from several basins, including Bakken, Eagleford, Niobrara, Alpine, Poland, Canol, Duverney, Permian, Canning, Columbia, Szechuan and Deepwater, including data from more than 30 wells.

The database contains the quality controlled rock mechanics properties that are sorted and organized by well depth and by compositional facies type. A company acreage interactive map was used to locate the mechanical test data for the basin under study. Any core data available is then posted to these links. Mechanical facies models are tested and vetted with the asset Geologists.

For the cuttings application, we ran the compositional facies model to characterize the nine rock types for each basin. The described mudstone ternary diagram was used globally, for all organic mudrock plays, to group the mechanical test data into the compositional facies rock types, but as noted above, the model can be updated or varied.

Using our sample selection methodology, we target multiple samples from similar rock types in the pilot whole cores, to validate repeatable mechanical response and assess parameter uncertainty. We rarely core a well that intersects all nine rock-types but we typically obtain multiple samples within a rock type. By grouping the samples, we derive the average mechanical response with uncertainty (or standard deviation to the mean) for each compositional facies.

In the prescribed mudstone ternary diagram shown in FIG. 2, we have plotted the results from four wells each from a different basin. The Tebo well is from the Niabrara basin, Uberwachen from the Bakken basin, Koopmann from the Eagleford basin and the Alpine core from the Alpine basin in Northern Alaska. Each dot on the ternary diagram represents the XRD mineral composition result from the individual mechanical bulk samples.

The mechanical data is grouped together (for each core) and averaged for each compositional facies. Within a basin, the compositional facies model yields mechanical properties with acceptable uncertainties.

A typical rock mechanical characterization is shown in FIG. 3, which displays a mechanical characterization for three mechanical parameters: 1) Young's modulus, 2) Poisson's Ratio and 3) Unconfined Compressive Strength over four cores (Tebo, Uberwachen, Koopmann & CD4-213A). The data is organized and sorted by the compositional facies and displayed in the center track. The mechanical properties vary by facies, but are predictable within a basin (i.e. they fall within a predictable range based on the bulk sample mechanical test results). The standard deviation of the material property is represented with the error bar—larger error bars indicate higher variation of mechanical response within a rock type, smaller error bars indicate lower uncertainties.

By adding additional cores to a basin analysis we can systematically apply statistical analysis techniques to properly determine the uncertainty associated with the mechanical parameters for a specified compositional facies. Our test results so far have demonstrated that within a basin, the mechanical properties will group with acceptable standard deviations using the ternary composition facies model as described herein.

5. Compare Cuttings Data with Database and Estimate Rock Mechanical Properties from Nearest Datapoints The cuttings data is then compared against the database of core data, and the mechanical rock properties from the closest datapoints in the database are then imputed to the cuttings. Thus, rock mechanical properties are assigned to the cuttings based on having the same depth and percentage of silicate, carbonate and clay as those core samples in the database.

6. Building a Material Property Log Using Petrophysical Techniques

The final step in the method is to pull all the pieces together using a petrophysical platform to create a wellbore answer product. A material property log is created from cuttings analysis. The log plots the mineral composition from XRD or similar analysis and the composition facies rock type. In parallel, the platform tracks the rock mechanical properties that would be displayed including static Young's modulus, static Poisson's ratio, unconfined compressive strength, cohesion, angle of internal friction, tensile strength, fracture toughness, elastic anisotropy, strength anisotropy, etc. together with their uncertainties (error bars).

The Petrophysical mechanical property log could take the following format:
  1D depth based mechanical log model—static elastic & failure properties
  1D facies based mechanical model—static elastic & failure properties
  2D facies based mechanical stratigraphy model—elastic, failure and geological heterogeneities that might influence mechanical rock strength
  Laminations
  Natural fractures
  Foliation plane The estimated rock properties that are generated in the inventive method can be used in any number of commercially available platforms for a variety of geophysical applications. For example, Hemispherical Matlab Application, GeoRock 3D, GeoRock 3D, GMS—GeoMechanical Survey, Coupled flow simulators with rock mechanics, such as ATH2VIS, TOUGH-FLAC, THAMES, MOTIF, FRACON, ROCMAS, FRT-THM, FEMH, GeoSys/Rockflow, FRACture, GEOCRACK, ABACUS, VISAGE, STARS by ZCMS.

The advantages of deriving rock mechanical properties from drill cuttings included:

1. Rock mechanical properties are obtained without interfering with the drilling process or increasing operational time. Rock cuttings are collected and depth referenced during the drilling process. Analysis can be performed at the rigsite or back in the lab—depending on the application.

2. Rock mechanical properties are obtained without increasing drilling cost for LWD or wireline data. The alternative method of obtaining mechanical rock properties is to use LWD or wireline log data, which adds additional cost to the drilling operation.

3. Rock mechanical properties are obtained without increasing drilling risk; for example increased risk of non-productive drilling time associated with downhole LWD or wireline tool failure. When running LWD or wireline logs in horizontal wells there is increased non-productive time risk because these tools have high tool failure rates in horizontal wells.

4. Rock mechanical properties are obtained without relying on the elastic model using sonic data. Mechanical properties derived from log data (LWD or wireline) assumes the formation is perfectly elastic (CHILE), which is an over-simplified model of true rock behavior, and thus leads to inaccuracies in heterogeneous rock.

5. Rock mechanical properties are obtained without the interpretation uncertainties associated with sonic tool physics issues in horizontal wells. Sonic logging physics was developed in vertical wells using near wellbore layer symmetry principles. In horizontal wells, the layer symmetry disappears and sonic logging physics becomes extremely complex. No one in industry has been able to solve this problem.

6. Rock mechanical properties can be obtained from any well in a basin (providing that pilot well mechanical characterization is already available or is obtained at or about the same time) from remnant drill cuttings. This is probably the strongest advantage of developing this technique. Drill cuttings are collected on all wells drilled by a company, providing a data driven method for determining material properties when no other cost effective option exists.

7. Rock mechanical data can be used to perform well diagnostics in horizontal wells with no other data. During hydraulic fracturing in horizontal wells, the engineer is sometimes faced with explaining why some wells, or intervals within a well, perform differently than others. Using wellbore cuttings, the engineer will be able to re-construct the near wellbore mechanical profile to diagnose the problem. Additionally, wellbore stability issues in horizontal wells are hard to predict. Once an instability occurs, wellbore drill cuttings can be used to re-construct the mechanical profile to help explain the cause(s) of the instability.

8. Rock mechanical properties can be used to constrain a 2D mechanical stratigraphy model. New horizontal well technology is being developed to create a 2 dimension stratigraphic layer models from gamma ray ("GR") and resistivity data run with LWD under the product name "BoreSight" (other vendor LWD forward modeling algorithms are also available). BoreSight was originally developed for geosteering applications. The framework (TVD depth, thickness and dip) of the stratigraphic layers are forward modeled with LWD data, while the material properties of the layers would be derived from the cuttings analysis described herein. Using this novel cuttings analysis, the modeled stratigraphic layer model could be properly constrained and populated.

9. The complete constitutive response can be modeled along any horizontal wellbore. The drill cuttings are analyzed for mineral composition and related back to core samples with similar mineral composition that have also been mechanically characterized in nearby offset vertical pilot wells. The mechanical characterization of the compositional facies includes a full constitutive response characterization. Therefore, once we have determined which rock type we are in, we can predict the complete constitutive response from core test results.

10. A realistic subsurface material property model (DIANE) can be constructed including the elements of geological heterogeneity. The goal is to develop a geologically conditioned mechanical framework model that explains the Discontinuous, Inhomogeneous, Anisotropic and Non-Linearly Elastic behavior of real subsurface rock mass. We can achieved this objective be including the individual elements of geological heterogeneity including:

i. Rock Type heterogeneity—From mechanical facies characterization ii. Stratigraphic heterogeneity—From 2D layer modeling using BoreSight iii. Structural Heterogeneity—From fracture and fault characterization using a variety of data including: outcrop analogs, seismic data, LWD image data, natural fracture characterization from core observation, etc.

Deriving rock mechanical properties from drill cuttings is important for characterizing the mechanical properties along a horizontal wellbore for drilling and completions engineering design needs. Mechanical properties are required for calibrating engineering stress models like frack gradient models assuming a CHILE subsurface material medium.

To model realistic near wellbore mechanical properties of DIANE material, we must include rock type characterizations in the context of layer models to properly describe the medium. Rock type characterization also includes the development of preferred subsurface failure mechanisms by facies. Understanding the preferred (most likely) failure mechanism will help us predict if a rock will preferentially fail in tension, shear or along a pre-existing foliation plane. Natural fracture, laminations and weak bedding planes are examples of foliation planes that exist in the subsurface. Rock type models (compositional facies models) can be used to determine the likelihood of subsurface failure mechanisms for a given load condition based on the composition and texture of the sample.

Examples of subsurface loading conditions:

1. Drilling a Horizontal Well

Currently, 75% of all wells drilled (globally) in ConocoPhillips are horizontal in design. Drilling horizontal wells can be hazardous because there is always a risk of borehole instability and collapse. This is typically true when drilling the build section (transitioning from a vertical to horizontal well) and in the horizontal section itself. Drillers often have no means to analyze borehole collapse problems and are forced to guess at their cause. Drill cuttings analysis would help them re-construct a subsurface model to assess mechanical failure issues and design better mud weight options on future wells.

In build sections, borehole failure analysis would be performed in the context of understanding preferred failure mechanisms by rock type. Weak, laminated shales can be characterized and understood by relating their rock failure properties to their composition. Then, with cuttings analysis, drillers could predict the high-risk intervals of the drill path and plan for them appropriately—avoiding them where possible or designing a completion that accounts for the higher risk.

2. Hydraulically Fracturing a Horizontal Well

Most horizontal wells are hydraulically fractured, which creates a unique subsurface (stress) loading condition that requires numerical modeling methods to resolve. Currently, most completions engineers model the near wellbore loading using a CHILE model. Unfortunately, real subsurface rock does not necessarily obey the CHILE model assumptions. Hydraulic fracture geometry generated from CHILE assumptions (i.e. planar frack models) have high uncertainty.

The only way to systematically reduce the uncertainty in planar frack model geometries is to develop realistic layer models that allow for the inclusion of known geological heterogeneities (i.e. build a DIANE model). The DIANE model would be informed by the analysis of the drill cuttings. A rock facies model would include a qualitative understanding of preferred failure mechanism of a facies type along the wellbore. Understanding preferred rock failure mechanisms would help the completions engineer by:

1. Avoiding compositional facies rock types that are resistant to hydraulic fracture breakdown, which, if encountered, would increase surface horsepower costs and increased risk of screenout.

2. Determining the ideal horsepower to breakdown a formation based on rock strength (measured and characterized with offset well whole core).

3. Designing the ideal frack recipes for each basin and performing comparative analysis across various basins with material property differences and layering understood.

4. Understanding how compositional facies predict failure mechanisms like:

Weak 'easy to frack' facies

Strong well cemented litho-facies requiring additional frack pressure

Facies with natural fractures that are prone to slip

Facies with inter-bedded layering that may influence frack propagation direction Facies that are highly laminated with high elastic & strength anisotropic Facies with other foliation planes—at preferred orientations.

The following references are incorporated by reference in their entirety for all purposes:

US20150152724, "Core sample testing protocol"

US20140373616, "Mechanical characterization of core samples"

US20170022808, "MICROMECHANICAL ELASTIC PROPERTIES SOLVER"

What is claimed is:

1. A method of estimating rock properties, said method comprising:

a) obtaining a plurality of rock cutting samples during drilling a horizontal well in a reservoir, wherein each cutting sample is lag corrected and assigned a depth $D_{1-n}$, wherein n is the number of cutting samples, and D is the depth of each cutting sample;

b) measuring a percentage content of silica, clay and carbonate of each of said cutting samples;

c) plotting or organizing said percentage content of silica, clay and carbonate on a ternary diagram or its equivalent for each of said cutting samples, said ternary diagram having three vertices and 0-100% of silica, clay and carbonate at the three vertices;

d) comparing against a database of rock mechanical properties obtained by measuring a plurality of core samples from offset vertical wells in said reservoir, said database organized by percentage content of silica, clay and carbonate;

e) estimating rock mechanical properties of said cutting samples from core samples having a same percentage content of silica, clay and carbonate, and imputing rock mechanical properties from said core samples to said cutting samples;

f) grouping all silica, clay and carbonate data into compositional facies based on the percentage content of silica, clay and carbonate; and g) constructing a continuous material property log along well depth, wherein the compositional facies are assigned to each depth along said well depth, and each compositional facies is populated with the imputed rock mechanical properties for that compositional facies.

2. The method of claim 1, further comprising inputting said material property log into a reservoir modeling program to predict reservoir performance and optimize a reservoir production plan, and thereafter implementing said plan in said reservoir to produce oil.

3. The method of claim 1, wherein said material property log plots the assigned composition facies and in parallel plots the imputed rock mechanical properties together with uncertainties.

4. The method of claim 1, wherein said cutting samples are obtained from drilling horizontal wells.

5. The method of claim 1, wherein said core samples are obtained by coring nearby vertical wells.

6. The method of claim 1, wherein said core samples were obtained by coring nearby vertical wells before step a).

7. The method of claim 1, wherein said core samples were obtained by coring nearby vertical wells at about the same time as step a).

8. The method of claim 1, wherein said rock mechanical properties include one or more of Young's modulus, Poisson's ratio, unconfined compressive strength, friction angle, cohesion, tensile strength, fracture toughness, peak strength, and compressibility.

9. The method of claim 8, further comprising inputting said rock mechanical properties of said cutting samples into a reservoir modeling program to predict reservoir performance and optimize a reservoir production plan.

10. The method of claim 9, further comprising using the optimized reservoir production plan to produce oil from said well in said reservoir.

11. The method of claim 1, further including the step of plotting said percentage content of silica, clay and carbonate of said cutting samples on a ternary diagram or its equivalent for each cutting sample, said ternary diagram having three vertices and 0-100% of silica, clay and carbonate at the three vertices and assigning a compositional facies based on where a cutting sample falls on the ternary diagram or its equivalent, wherein said ternary diagram is subdivided into nine compositional facies using the following cutoffs (+/- 3%):
  i) Limestone >85 Carbonate
  ii) Marly Limestone >65% Carbonate <85%
  iii) Argillaceous Marl >35% Clay, <65% Carbonate >35%, <10% Silica
  iv) Marl >35% Carbonate <65%, >10% Silica >10% Clay
  v) Siliceous Marl >35% Silica, <65% Carbonate >35%, <10% Clay
  vi) Claystone >65% Clay
  vii) Calcareous Mudstone <35% Carbonate >15%, >10% Silica <65%, >10% Clay <65%)
  viii) Siliceous Mudstone >65% Silica
  ix) Mudstone <15% Carbonate, <65% Silica, <65% Clay.

* * * * *